United States Patent [19]

Pioch

[11] 4,375,547

[45] Mar. 1, 1983

[54] N-METHYL-N'-2-([(2-DIMETHYLAMINOME-THYL)-4-THIAZOLYL]METHYLTHI-O)ETHYL 2-NITRO-1,1-ETHENEDIAMINE

[75] Inventor: Richard P. Pioch, Indianapolis, Ind.

[73] Assignee: Eli Lilly and Company, Indianapolis, Ind.

[21] Appl. No.: 193,192

[22] Filed: Oct. 2, 1980

[51] Int. Cl.$^3$ .................. C07D 277/20; A61K 31/425
[52] U.S. Cl. .................................... 548/205; 548/204; 424/270
[58] Field of Search ................ 548/204, 205; 546/209; 544/106; 260/313.1

[56] References Cited

U.S. PATENT DOCUMENTS

| | | | |
|---|---|---|---|
| 3,853,865 | 10/1974 | Brenner et al. ...................... | 548/204 |
| 3,917,593 | 11/1975 | Loev .................................... | 546/409 |
| 4,022,797 | 5/1977 | Durant et al. ........................ | 548/204 |
| 4,061,637 | 12/1977 | Manghisi et al. .................... | 260/268 |
| 4,137,237 | 1/1979 | Durant et al. ........................ | 260/308 |
| 4,166,856 | 9/1979 | Durant et al. ........................ | 424/270 |
| 4,173,644 | 11/1979 | Brown et al. ........................ | 424/270 |
| 4,191,769 | 3/1980 | Durant et al. ........................ | 424/263 |
| 4,200,578 | 4/1980 | Algieri et al. ........................ | 548/193 |
| 4,242,350 | 12/1980 | Yellini et al. ........................ | 424/270 |
| 4,252,819 | 2/1981 | Hirata et al. ........................ | 424/285 |
| 4,256,752 | 3/1981 | Bebenburg et al. ................. | 424/263 |
| 4,285,952 | 8/1981 | Durant et al. ........................ | 424/263 |

FOREIGN PATENT DOCUMENTS

| | | | |
|---|---|---|---|
| 1421792 | 1/1976 | United Kingdom ................ | 548/205 |
| 2003471 | 3/1979 | United Kingdom ................ | 548/204 |

Primary Examiner—Donald G. Daus
Assistant Examiner—G. Hendricks
Attorney, Agent, or Firm—James L. Rowe; Arthur R. Whale

[57] ABSTRACT

N-Alkyl-N'-([2-(aminoalkyl)-4-thiazolylmethyl]thioalkyl) guanidines, thioureas, ethenediamines and related compounds, $H_2$ receptor antagonists, useful in inhibiting gastric acid secretion in mammals.

1 Claim, No Drawings

N-METHYL-N'-2-([(2-DIMETHYLAMINOME-THYL)-4-THIAZOLYL]METHYLTHIO)ETHYL 2-NITRO-1,1-ETHENEDIAMINE

BACKGROUND OF THE INVENTION

Reaction of a nitrile with ammonia or an amine leads to the formation of an amidine. In the simplest case, reaction, for example, of acetonitrile with ammonia yields acetamidine, $$CH_3-\underset{\underset{NH_2}{\|}}{C}-NH_2,$$

the analogue of acetic acid in the liquid ammonia solvent system. Reaction of cyanamide $H_2NCN$ with an amine $RNH_2$ yields an aminoamidine or guanidine $$NH_2-\underset{\underset{NH}{\|}}{C}-NH-R.$$

Reaction of an amine ($RNH_2$) with potassium isothiocyanate yields a mercapto-amidine, more commonly known as an isothiourea, $$HS-\underset{\underset{NH}{\|}}{C}-NHR,$$

which structure can tautomerize to a thiourea, $$NH_2-\underset{\underset{S}{\|}}{C}-NHR.$$

Ethenediamines of the formula, $$NH_2-\underset{\underset{HC-R^1}{\|}}{C}-NHR,$$

can also be looked upon as substituted amidines, since a tautomer of the above formula would have the following structure $$HR^1CH-\underset{\underset{NH}{\|}}{C}-NHR.$$

All of the above substituted amidines—thioureas, guanidines, and ethenediamines—form part of the chemical structure of a new group of histamine H$_2$-receptor antagonists useful in treatment of peptic ulcer.

One of the first chemical compounds to be recognized as a powerful H$_2$-receptor antagonist useful in the treatment of peptic ulcer was a thiourea, burimamide, N-methyl-N'-(4-[4(5)-imidazolyl)]butyl)thiourea, having the following formula:

BURIMAMIDE

The properties of this compound are disclosed in the *Pharmacological Basis of Therapeutics*, Goodman & Gilman 5th Ed. (MacMillan Publishing Co., Inc., New York) page 612.

A second generation of histamine H$_2$-receptor antagonists involved compounds developed by Black, Durant and co-workers with a structure more or less similar to the above but in which there was a permissible interrupting group—oxygen, sulfur or NH—in the alkyl side chain attached to the hetero ring. The most prominent of these compounds has been cimetidine, chemically N-cyano-N'-methyl-N"-[2-([(5-methyl-1H-imidazol-4-yl)methyl]thio)ethyl]guanidine represented by formula II below:

CIMETIDINE

A large number of patents based upon four original filings (Ser. Nos. 230,451; 284,992, 384,993; and 385,027) have issued to Durant et al including the following issued U.S. Pat. Nos. 3,950,333; 4,049,672; 4,022,797; 4,137,237; 4,024,271; 4,070,475; 4,154,844; 3,905,984; 4,027,026; 3,932,427; 4,018,928; 3,950,353; 4,053,473; 4,018,931; 4,069,327; 4,151,288; 4,000,296; 4,083,988; 4,129,657; 4,098,898; 4,166,856; 4,072,748; 3,971,786; 4,060,620; 3,876,647; 3,920,822; 3,897,444; and 3,975,530.

Other disclosed ring systems in addition to imidazole include pyrazole, pyridine, pyrimidine, pyridazine, thiazole, isothiazole, oxazole, isoxazole, triazole, thiadiazole, benzimidazole and tetrahydroimidazo[1,5-a]pyridine, with the greatest emphasis being placed on compounds having an imidazole ring system. Groupings which may be present at the terminal end of the alkyl or alkylthioalkyl bridging group include guanidine, cyanoguanidine, urea, ethenediamine and thiourea.

The above list of numbered patents to Durant and co-workers is not exhaustive since several patents may have issued as divisions of a single parent. Each of these divisions has, of course, an identical disclosure to its parent and it is believed that the above list is a fair representation of the Durant et. al., patents.

Patents referring to thiazole or oxazole ring systems are of particular relevance to this invention. The two basic disclosures by the Durant groups are contained in U.S. Pat. No. 3,950,333 and U.S. Pat. No. 3,950,353; both of these are continuations-in-part of Ser. No. 290,584 which was in turn a continuation-in-part of Ser. No. 230,451. In U.S. Pat. No. 3,950,333, the disclosure relating to thiazoles begins at Example 115, column 37. Thiazoles substituted with a chloro or an alkyl group are described. The thiazole nucleus is then attached at the 2- or 4-position of the thiazole ring to an alkylthioalkyl side chain terminating in an N-cyano-N'-methylguanidine. This disclosure is followed by similar disclosures for isothiazoles, oxazoles and isoxazoles. The disclosure in U.S. Pat. No. 3,950,353 relating to thiazoles begins at Example 110, column 37. Here, substantially the same thiazole nucleus is attached to an N-methylthiourea. A similar disclosure is present for isothiazoles, oxazoles and isoxazoles. U.S. Pat. No. 4,022,797, a division, specifically claims the cyanoguanidine derivatives and U.S. Pat. No. 4,137,234, another division, specifically claims thioureas.

U.S. Pat. No. 4,000,296 discloses and claims a group of N-alkyl or N-arylsulfonyl-N′-alkyl-N″(heterocyclealkylthioalkyl)guanidines in which the heterocycle can be thiazole, isothiazole, oxazole or isoxazole. Alkyl, alkylaminoalkyl and alkyloxyalkyl bridging groups (connecting the heterocyclic to the substituent amidine group) are also disclosed. Substituted heterocycles belonging to any of the above classes are not disclosed. U.S. Pat. No. 4,166,856, originating with the Durant group, discloses and claims a number of imidazoles and thiazoles carrying the usual alkylthioalkyl-guanidine, -thiourea or -ethenediamine side chain, which is invariably in the 2-position of the ring. The N′-nitrogen can be substituted with groups other than alkyl including allyl, phenylethyl, 2,2,2-trifluoroethyl, etc. The thiazole ring may also be substituted by alkyl, hydroxy, halogen or amino.

Another group of investigators under Yellin has disclosed—see U.S. Pat. Nos. 4,165,377 and 4,165,378—certain novel thiazoles having a side chain such as that discussed above attached at the 4-position of the thiazole ring; i.e., an alkylthioalkyl-guanidine, -ethenediamine or -thiourea group attached thereto but also bearing a guanidino group in the 2-position. Alkylene, alkenylene and alkyloxyalkyl bridging groups are also disclosed. A representative compound is 2-guanidino-4-[2-(2-cyano-3-methylguanidino)ethylthiomethyl]thiazole which is said to have greatly increased activity over cimetidine.

A third research group at Allen and Hanbury Ltd. has prepared compounds with a furan ring carrying the standard alkylthioalkyl (or alkyloxyalkyl or alkyl) side chain terminating in a substituted guanidine or ethenediamine group, and also having a dialkylaminoalkyl substituent attached at a second position in the furan ring—see U.S. Pat. Nos. 4,128,658 and 4,168,855. Belgian Pat. Nos. 867,105 and 867,106 disclose the corresponding thiophene and aminoalkylbenzenes. Several of the compounds thus produced had a greater activity than cimetidine.

Finally, a research group at Bristol-Myers have issued two United States patents involving different heterocycles. The first of these, U.S. Pat. No. 4,203,909, relates to furans carrying an alkylthioalkyl-guanidine (or thiourea or ethenediamine) side chain in the 2-position and an aminoalkyl side chain in the 5-position. However, it is a requirement of these structures that the N′-nitrogen carry only an alkynyl group. One of the compounds, 1-nitro-2-(2-propynylamino)-2-(2-[(5-dimethylaminomethyl-2-furyl)methylthio]ethylamino)ethylene, is said to have 7.45 times the activity of cimetidine in a standard H₂ receptor assay. The second patent, U.S. Pat. No. 4,200,578, covers broadly thiazoles substituted with an alkylthioalkylguanidine (or thiourea or ethenediamine) side chain, but again carrying an obligatory alkynyl group on the N′-nitrogen. Other permissible substituents in the thiazole ring include alkyl, guanidino or aminoalkyl. Despite the broad disclosure, the actual working examples are limited to thiazoles carrying the alkylthioalkylguanidine, etc. side chain in the 2-position of the thiazole ring except for a few compounds in which the side chain is carried in the 4-position, and there is an obligatory guanidino group in the 2-position. Synthetic Schemes I through VIII of the patent are suitable only for preparing 2-substituted thiazoles. Example 22 discloses thiazoles substituted in the 4-position but these thiazoles either do not carry a second ring substituent or, if there is one, it is a guanidino group in the 2-position. In the H₂ receptor assay, the most active compounds disclosed had an activity less than twice that of cimetidine.

To summarize, thiazoles in which there is a 4-alkylthioalkyl(or alkyl)-guanidine (or thiourea or ethenediamine) side chain are known wherein the thiazole group can be substituted in the 2- or 5-position with guanidino, methyl, chloro and aminoalkyl. The disclosure relating to thiazoles substituted with an aminoalkyl group at one position in the thiazole ring and, at a second position, a bridging alkylthioalkyl, alkylene, alkenylene or alkyloxyalkyl group terminating in a substituted amidine group, is restricted to amidines carrying a N-alkynyl group as part of the terminal grouping.

SUMMARY OF THE INVENTION

This invention provides compounds of the formula

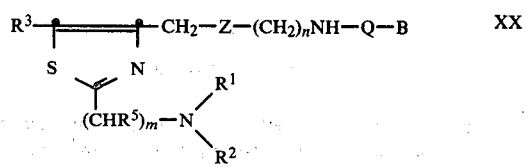

wherein each of $R^1$ and $R^2$ are individually H or $(C_1-C_3)$alkyl, one of $R^1$ and $R^2$ can be benzyl or benzoyl, and when taken together with the nitrogen to which they are attached, represent piperidino, pyrrolidino or morpholino; except that only one of $R^1$ and $R^2$ can be H when Z is $CH_2$;

$R^3$ is H or $(C_1-C_3)$alkyl;

Z is O, S, SO or $CH_2$;

n is 2 or 3 when Z is O, S or SO and n is 1, 2 or 3 when Z is $CH_2$;

$R^5$ is H or $CH_3$;

m is 1, 2 or 3;

Q is

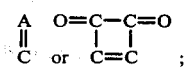

wherein A is N-CN, N-NO₂, CH-NO₂, S, O, NH, N-SO₂-aryl, N-SO₂-(C₁-C₃)alkyl, N-CO-NH₂, N-CO-(C₁-C₃)alk, N-CO₂-(C₁-C₃)alk; CH-SO₂-aryl or CH-SO₂-CH₃, wherein aryl is phenyl, halophenyl, (C₁-C₃)alkylphenyl or (C₁-C₃)alkyloxyphenyl; and B is NH-R when Q is

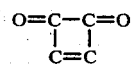

and NH-R or YR⁴ when Q is

wherein Y is S or O and R is H or $R^4$ wherein $R^4$ is $(C_1-C_5)$alkyl, $(C_3-C_6)$ cycloalkylmethyl, hydroxy$(C_1-C_5)$alkyl, $(C_3-C_6)$cycloalkyl or alkyloxyalkyl or dialkylaminoalkyl wherein the total number of carbons is less than 8; and there is at least a two carbon chain between the hetero atoms and pharmaceutically acceptable acid addition salts thereof.

Bases falling within the scope of the above formula include:

N-ethyl-N'-[2-(2-dimethylaminoethyl)-5-methyl-4-thiazolyl)methylthio]ethylguanidine N-cyclopropylmethyl-N'-(3-([(2-(methylethylaminomethyl)-4-thiazolyl)]methylthio)propylguanidine.

N-cyclohexyl-N'-[2-(2-aminomethyl-5-n-propyl-4-(thiazolyl)methylthio]ethyl-N''-nitroguanidine N-cyclobutylmethyl-N'-[(2-(diethylaminoethyl)-4-thiazolyl]methylthio)ethyl-N''-p-chlorophenylsulfonylguanidine N-n-propyl-N'-2-([2-(methylaminomethyl)-5-methyl-4-thiazolyl]methylthio)ethylthiourea N-isopropyl-N'-3-([2-(ethylaminoethyl)-5-ethyl-4-thiazolyl]methylthio)propylguanidine N-ethyl-N'-2-([2-(diethylaminopropyl)-5-methyl-4-thiazolyl]methylthio)ethyl 2-(o-bromophenylsulfonyl)-1,1-ethenediamine or [1-(o-bromophenylsulfonyl)-2-ethylamino-2-(2-([2-di ethylaminopropyl)-5-ethyl-4-thiazolyl]methylthio)ethylamino)ethylene N-cyclopentylmethyl-N'-2-([2-(isopropylaminomethyl)-4-thiazolyl]methylthio)ethyl 2-methanesulfonyl-1,1-ethenediamine N-pentyl-N'-3-([2-(diethylaminoethyl)-5-propyl-4-thiazolyl]methylthio)propyl 2-nitro-1,1-ethenediamine.

N-(3-methylbutyl)-N'-2-([2-(n-propylaminomethyl)-5-ethyl-4-thiazolyl]methylthio)ethyl 2-o-tolylsulfonyl-1,1-ethenediamine N-isobutyl-N'-2-([2-(ethyl-n-propylaminomethyl)-5-n-propyl-4-thiazolyl]methylthio)ethyl 2-nitro-1,1-ethenediamine, N-n-propyl-N'-2-[(2-piperidinomethyl-4-thiazolyl)methylthio]ethyl-N''-cyanoguanidine N-methoxyethyl-N'-3-([2-(aminomethyl)-4-thiazolyl]-methylthio)propyl 2-nitro-1,1-ethenediamine N-(3-hydroxypropyl)-N'-4-[2-(ethylaminomethyl)-5-methyl-4-thiazolyl]-1-butyl-N''-cyanoguanidine N-cyclobutylmethyl-N'-5-[2-(dimethylaminomethyl)-4-thiazolyl]pentyl 1,2-diamino-3,4-dioxo-1-cyclobutene or 1-(5-(2-(dimethylaminomethyl)-4-thiazolyl)pentylamino)-2-cyclobutylmethylamino-3,4-dioxo-1-cyclobutene N-cyclopentyl-N'-2-[(4-morpholinomethyl-5-ethyl-4-thiazolyl)methyloxy]ethylguanidine N-cyclohexyl-N'-3-([2-(1-pyrrolidinomethyl)-4-thiazolyl]methyloxy)propylurea.

N-cyclopropylmethyl-N'-3-([2-(methylaminopropyl)-4-thiazolyl]methyloxy)propylthiourea N-dimethylaminoethyl-N'-3-[2-(ethylaminoethyl)-4-thiazolyl]propylguanidine.

N-methyl-N'-3-([2-(diethylaminomethyl)-5-methyl-4-thiazolyl]methylsulfinyl)propyl-N''-nitroguanidine.

N-isopropyl-N'-2-([2-(di-n-propylaminomethyl)-4-thiazolyl]methylthio)ethyl-N''-methoxycarbonylguanidine N-2-methylbutyl-N'-5-[2-(diethylaminoethyl)-4-thiazolyl]pentyl-N''-acetylguanidine N-n-butyl-N'-4-[2-(1-pyrrolidino)methyl)-4-thiazolyl]-butyl-N''-aminocarbonylguanidine.

N-methyl-N'-2-([2-(4-morpholinomethyl)-5-methyl-4-thiazolyl]methylthio)ethyl 2-nitro-1,1-ethenediamine N-ethyl-N'-2-([2-(1-pyrrolidinomethyl)-4-thiazlyl]methylthio)ethyl 2-methanesulfonyl-1,1-ethenediamine and the like.

In Formula XX, the term $(C_1-C_3)$ alkyl includes methyl, ethyl, n-propyl or isopropyl. Thus, the term $(C_1-C_3)$alkylphenyl would include o, m and p-tolyl, o, m, and p-ethylphenyl and the like. Similarly, the term $(C_1-C_3)$alkoxyphenyl includes o, m, p-anisyl, o, m, and p-ethoxyphenyl and the like. The term halophenyl includes o, m, and p-chlorophenyl, bromophenyl, fluorophenyl and iodophenyl.

The term $(C_1-C_5)$alkyl includes all of the above $(C_1-C_3)$alkyl radicals plus n-butyl, isobutyl, sec.-butyl, t-butyl, n-amyl, isoamyl, 2-methylbutyl, 2-methyl-2-butyl and the like radicals. The term $(C_3-C_6)$cycloalkyl includes cyclobutyl, cyclopropyl, cyclopentyl, cyclohexyl, methylcyclopentyl and the like radicals.

Illustrative of the groups alkoxyalkyl or dialkylaminoalkyl having less than a total of eight carbons, and joined to the NH group by at least a two carbon chain which $R^4$ represents are 2-methoxyethyl, isopropoxyethyl, 3-ethoxy-2-methylpropyl, 2-(2-pentyloxyethyl) 2-dimethylaminoethyl, diethylaminoethyl, 2-methylpropylamino-2-propyl and the like.

The pharmaceutically-acceptable acid addition salts of the compounds of this invention include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Compounds according to XX above have at least one basic center, the aminoalkyl group at C-2 of the thiazole ring but may have a second or third basic salt-forming group. For example, the substituted amidine terminal group can also have nitrogens present which are, depending on the substitution pattern, sufficiently basic to form salts with nontoxic acids.

The compounds of this invention wherein Z is S or O—in other words, a heteroatom—are conveniently prepared from a 2-[(2-aminoalkyl-4-thiazolyl)methylheteroatom]alkyl amine. The preparation of these starting materials is illustrated in Flow Chart A below using a compound in which the heteroatom is sulfur for exemplary purposes only.

Flow Chart A

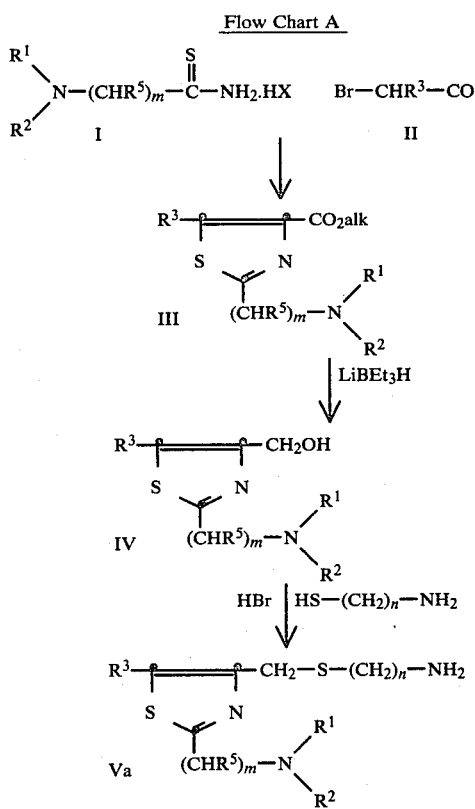

In the above Flow Chart, alk is conveniently methyl or ethyl and $R^1$, $R^2$, $R^3$, $R^5$, m and n have the same meaning as hereinabove.

In accordance with the above procedure, an acid addition salt of an aminoalkylthioacetamide (I) is reacted with a beta-bromo-alpha-ketoester (II) such as ethyl bromopyruvate ($R^3$=H) to yield an alkyl (methyl or ethyl) 2-(aminoalkyl)-4-thiazolecarboxylate (III). Reduction of this ester with a suitable hydride reducing agent such as lithium triethylborohydride, lithium aluminum hydride, sodium borohydride, diisobutylaluminumhydride and the like yields the corresponding hydroxymethyl compound (IV). Reaction of the 4-hydroxymethylthiazole with cysteamine or its higher homologue ω-thiopropylamine in the presence of acid yields directly a 2-[(2-aminoalkyl-4-thiazolyl)methylthio]alkylamine (Va) optionally substituted with an alkyl group in the 5-position of the thiazole ring.

In the process indicated in Flow Chart A, in going from IV to V, the hydroxymethyl group can be halogenated as with thionylchloride to yield a 4-chloromethylthiazole and this compound reacted with the sodium salt of the particular mercaptoalkylamine. In fact, any standard leaving group (a group labile to nucleophilic displacement) can be employed here in place of chloro in the chloromethyl side chain including for example p-tosyloxy, mesyloxy (methanesulfonyloxy), bromo, iodo and the like.

If it is desired to prepare the side chain oxygen analogue of Va (Z=O), a process utilizing 2-chloroethylamine or 3-chloropropylamine to react with the 4-thiazolemethanol, under basic conditions, can be employed as well as can the analogous Williamson ether process using the sodium salt of the hydroxyalkylamine with a 4-thiazolylmethyl halide.

Several pathways are available for preparing the compounds of this invention. These pathways or synthetic routes utilize an amine of the generalized formula

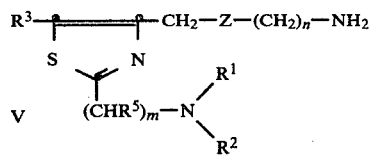

wherein Z is S, O or $CH_2$, as a starting material. These routes are illustrated in Flow Charts B, C and D below. According to Flow Chart B, a starting primary amine, the ultimate product of Flow Chart A (Va), (Z=S) is reacted with, for example, an N-alkyl, (cycloalkyl, cycloalkyl-substituted-alkyl, alkoxyalkyl or dialkylaminoalkyl) 1-methylthio-2-nitroethaneamine. During the reaction, the elements of methylmercaptan are displaced and the final desired product (VIIa) is an N-2-[(2-aminoalkyl-5-optionally-substituted-4-thiazolyl)methylthio]alkyl-N'-alkyl (cycloalkyl, cycloalkylalkyl, alkoxyalkyl or dialkylaminoalkyl) 2-nitro-1,1-diaminoethylene (or ethenediamine). Similarly, the primary amine (Va) can be reacted with an S-methyl-N-alkyl (cycloalkyl, cycloalkylalkyl, alkoxyalkyl or dialkylaminoalkyl)-N'-cyanoisothiourea to form the desired product (VIa)—an N-alkyl, (cycloalkyl, cycloalkylalkyl, alkoxyalkyl or dialkylaminoalkyl)-N'-2-[(2-aminoalkyl-5-optionally substituted-4-thiazolyl)methylthio]ethyl-N''-cyanoguanidine.

Flow Chart B

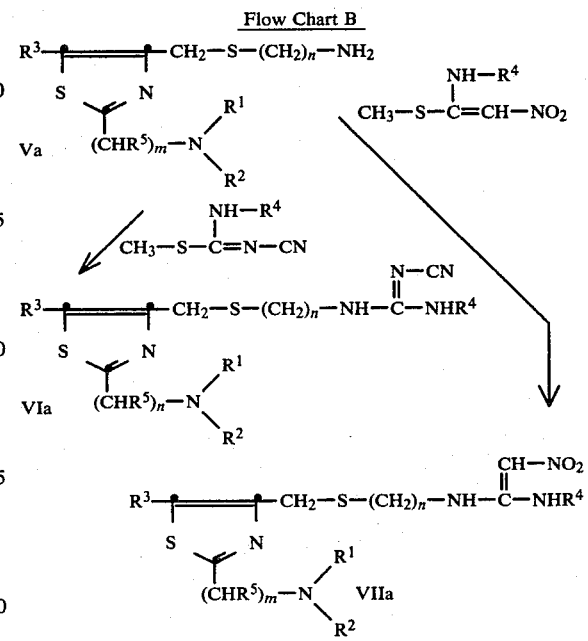

wherein $R^1$-$R^5$, m and n have the same meaning as hereinabove.

In the above reactions, it is apparent that in place of an N-alkyl etc.-1-methylthio-2-nitroethyleneamine, an N-alkyl etc. 1-methylthio-2-methylsulfonylethyleneamine (or 2-phenylsulfonylethyleneamine) could be used.

If it is desired to prepare a compound of structure XX wherein Q is

and A is N-SO$_2$-phenyl, the reagent used to prepare such N"-phenylsulfonylguanidines is dimethyl N-phenylsulfonylimidodithiocarbonate prepared by the general procedure of Ber., 99, 2885 (1966). The methylsulfonylguanidines are produced from a dialkyl N-methylsulfonylimidodithiocarbonate prepared in the same fashion. Similarly, it is apparent that an N-alkyl, (cycloalkyl, cycloalkylalkyl, hydroxyalkyl, alkoxyalkyl or dialkylaminoalkyl) 1-methylthio-2-arylsulfonylethyleneamine (or 2-methylsulfonylethyleneamine) could be used in place of the N-alkyl etc.-1-methylthio-2-nitroethyleneamine of the above flow chart. 2-Arylsulfonyl-1-methylthioethyleneamine, the intermediate containing a sulfonyl group, can be prepared by reacting, for example, a 2-aylsulfonyl-1,1-bis-methylthio-ethylene (prepared by the method of *Bull., Soc. Chem. Fr.*, 637, (1973)) with one mole of an amine NH$_2$R$^4$. The 2-methylsulfonyl derivatives useful as intermediates can be prepared in the same fashion.

Obviously, compounds corresponding to VI and VII in which O replaces S in the bridging group are prepared by substituting a 2-aminoalkyl-4-thiazolylmethyloxyalkylamine for Va in Flow Chart B.

An alternate method of preparation of the compounds of this invention is illustrated in Flow Chart C. According to this procedure, the same requisite thiazole intermediate (V) is reacted with a 1,1-bis-methylthio-2-nitro (or arylsulfonyl or methylsulfonyl) ethylene to produce an N-2-[(2-aminoalkyl-5-optionally-substituted-4-thiazolyl)methylthio]ethyl 1-amino-1-methylthio-2-nitro (or arylsulfonyl or methylsulfonyl)ethyleneamine.

Flow Chart C

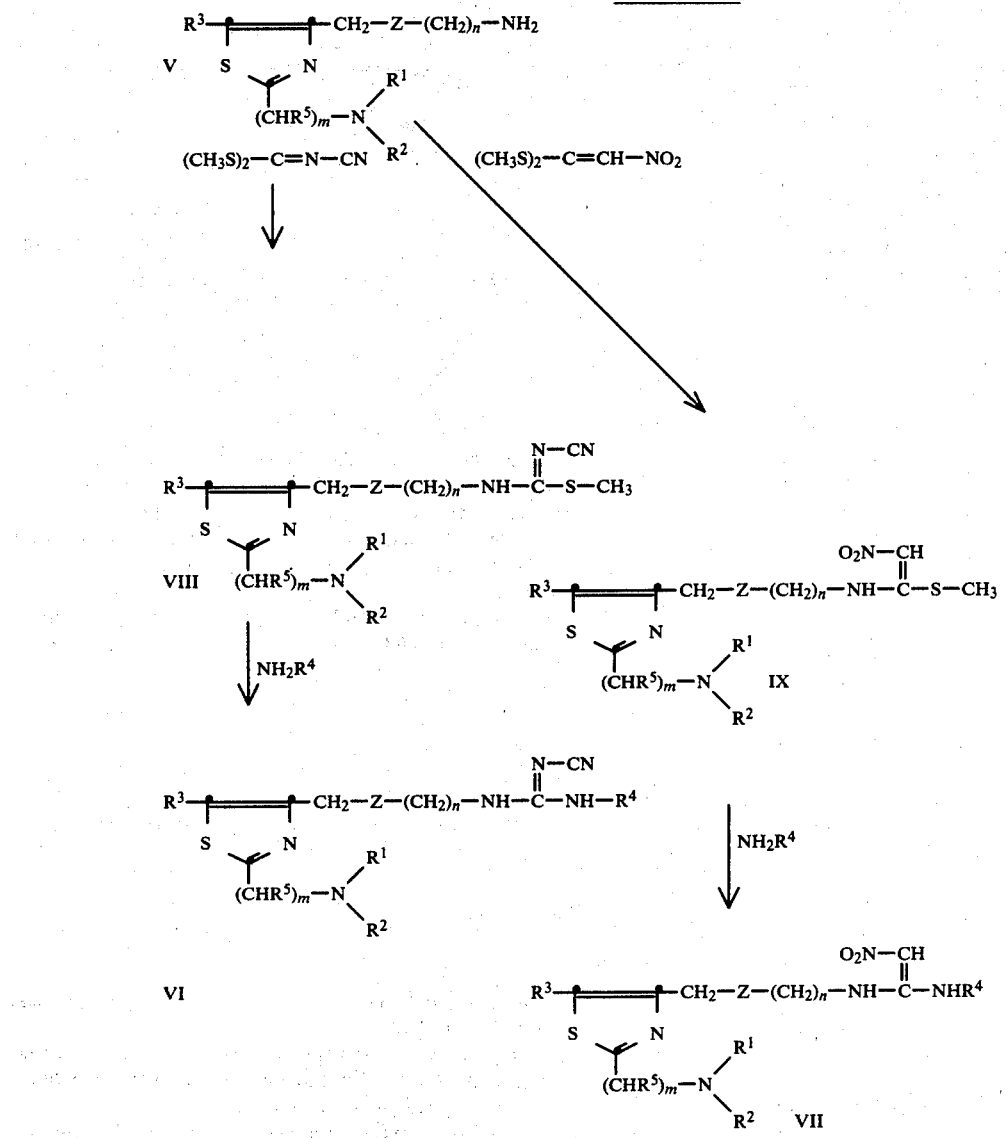

wherein Z, R$^1$-R$^5$, m and n have the same meaning as hereinabove.

According to Flow Chart C, reaction of the methylmercapto compound VIII or IX with a primary amine $NH_2R^4$ yields the desired product. For example, dimethylcyanodithioimidocarbonate will react with the thiazolylmethylthioalkylamine or other thiazolyl side chain amine V to produce an N-2-[(2-aminoalkyl-5-optionally-substituted-4-thiazolyl)methylthio]ethyl (or propyl)-S-Methyl-N'-cyanopseudothiourea (VIII where Z is S). Reaction of this compound with the primary amine $NH_2R^4$ again yields the desired product VI. Compounds in which A is $CH-NO_2$ etc. as in IX are prepared similarly and reacts similarly to yield an analogous final product having an ethenediamine terminal group as in VII.

Following the above procedure, in certain instances, a reactant such as VIII can be employed in which an $OCH_3$ group replaces the $SCH_3$. This methoxy group is replaceable by the amine $NH_2R^4$ as is the $S-CH_3$ group illustrated above. For example, a compound of the formula $(CH_3O)_2-C=A$ wherein A is N-CN can be employed.

As was the case with Flow Chart B, the procedures of Flow Chart C can be modified to produce compounds according to XX above in which Z is O by utilizing an appropriate starting material containing oxygen in the side chain.

A third type of compound coming within the scope of the above formula is a thiourea wherein A is S. The preparation of these compounds is illustrated in Flow Chart D.

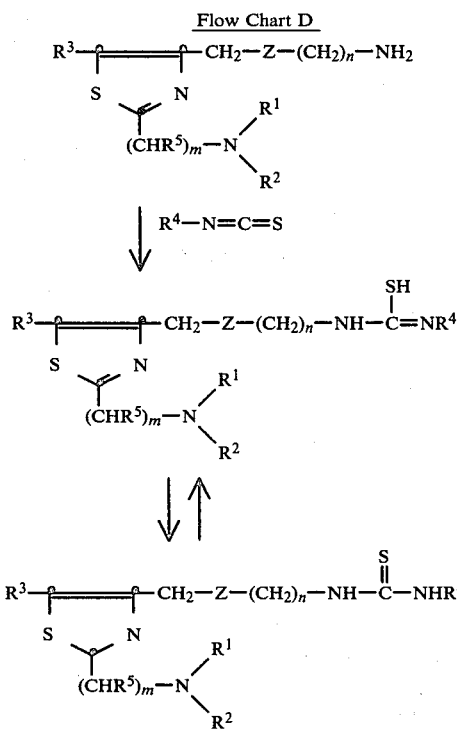

Flow Chart D wherein $R^4$, $R^1$, $R^2$, $R^3$, $R^5$, Z, n and m have their previously assigned meanings.

According to Flow Chart D, the starting amine, (V), for example a thiazolylmethylthioalkylamine (Z=S), is reacted with a suitably substituted isothiocyanate to yield directly the isothiourea (X) which compound is in equilibrium with the thiourea itself (XI). Similarly, an isocyanate, $R^4-N=C=O$, can be used to prepare the corresponding urea.

Compounds according to XX above in which Q is a 3,4-dioxo-1,2-cyclobutendiyl radical are prepared in a fashion more or less analogous to the preparation of the corresponding ethenediamines of Flow Chart C, in that a bivalent reacting group, 1,2-dimethoxy-3,4-dioxocyclobutene, is first reacted with a 2-aminoalkyl-4-thiazolylmethylthio(or oxy)alkyl amine to yield a 1-[2-aminoalkyl-4-thiazolylmethylthio(or oxy)]alkylamino-2-methoxy-3,4-dioxobutene. This latter compound is in turn reacted with a primary amine, $NH_2R^4$, (where $R^4$ has the same meaning as hereinabove) to yield the desired compound.

Compounds according to the above formula wherein B is $NH_2$ (i.e., B is NHR, R is H and A is NCN) can be prepared by a special reaction according to Flow Chart E.

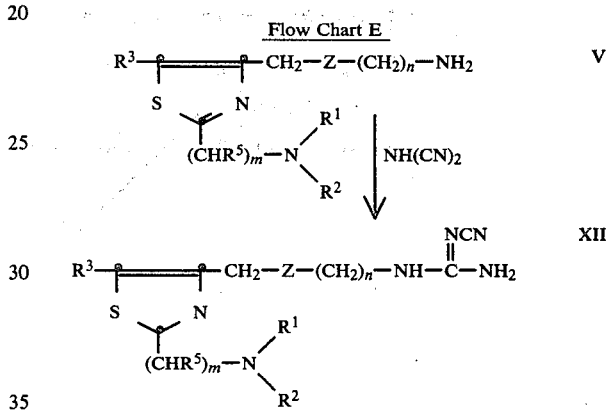

Flow Chart E wherein $R^1$, $R^2$, $R^3$, $R^5$, Z, n and m have then previously assigned value.

In this procedure, dicyanamide or one of its salts, preferably the sodium salt, is reacted with a thiazolyl primary amine (V) to yield the cyanoguanidine (XII) directly.

Compounds according to Formula XX above wherein A is $N-CO-NH_2$; i.e., having a terminal group of the structure

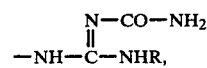

are prepared by hydration of the corresponding cyano compound,

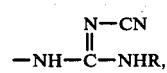

in dilute mineral acid as, for example, dilute aqueous hydrochloric acid.

Compounds according to Formula XX above in which Z is SO, a sulfinyl group, are prepared by oxidation of the corresponding thio derivative. An oxidizing agent such as sodium metaperiodate in a suitable solvent such as a lower alkanol-water mixture is conveniently employed.

Finally, many of the compounds of this invention can be readily repaired via a carbodiimide intermediate as illustrated in Flow Chart F.

Flow Chart F

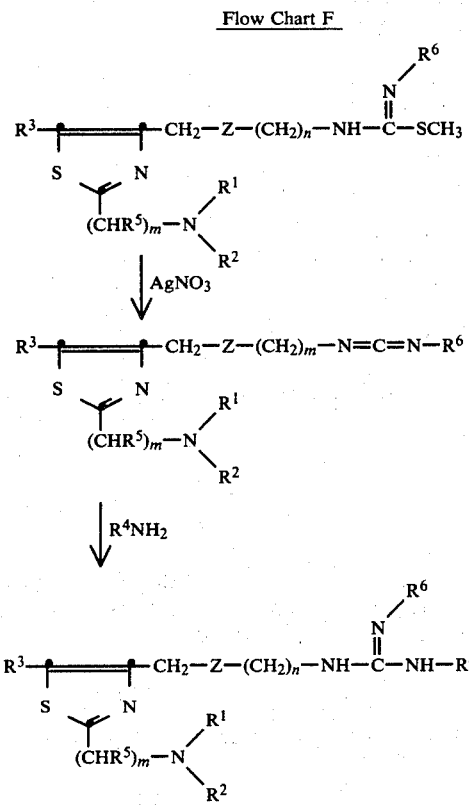

wherein R[1]-R[4], Z n and m have their previously assigned value and R[6] is CN, CO (C$_1$-C$_3$)alk, CO$_2$(C$_1$-C$_3$)alk, SO$_2$-aryl or SO$_2$CH$_3$ wherein aryl is phenyl, halophenyl, (C$_1$-C$_3$)alkylphenyl or (C$_1$-C$_3$)alkyloxyphenyl.

According to Flow Chart F, an isothiourea VIIIa (prepared by the procedure of Flow Chart C or equivalent procedure) is reacted with silver nitrate to prepare a carbodiimide (XIII), reaction of which with a primary amine, R[4]NH$_2$, yields those compounds of this invention wherein A is NCN etc. (VI).

Compounds according to the above formula (XX) wherein Z is CH$_2$ and n is 1, 2 or 3, can be prepared by the procedure illustrated in Flow Chart G below.

Flow Chart G

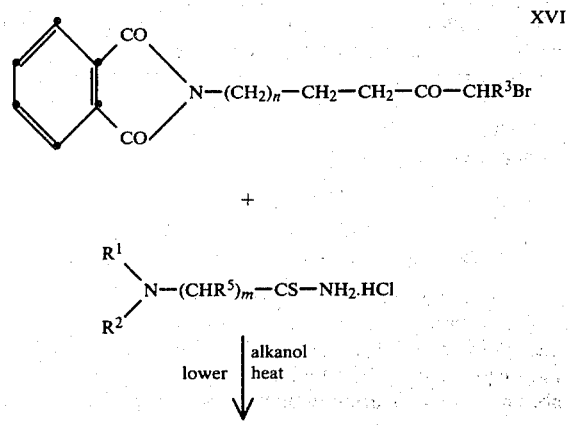

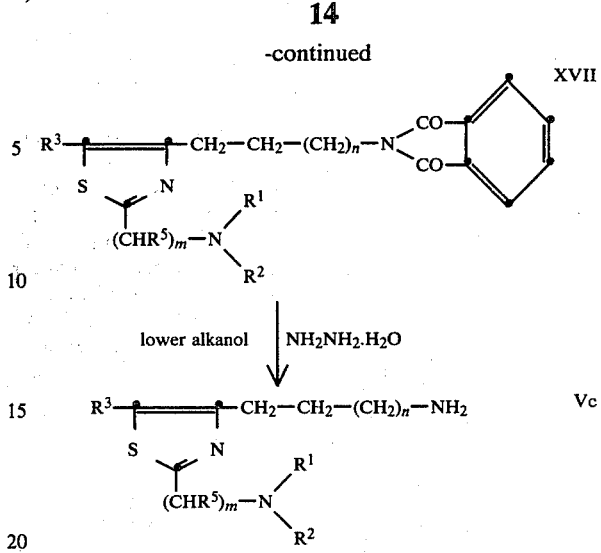

wherein R[1], R[2], R[3], R[5], n and m have their previously assigned meaning.

According to flow chart G, an omega (phthalimido)alkyl halomethyl ketone (XVI) is reacted with dimethylaminothioacetamide hydrochloride to produce a 2-aminoalkyl-5-permissibly substituted-4-omega-(phthalimido)alkylthiazole (XVII). The phthalimido group is removed by hydrolysis with hydrazine hydrate to produce the 4-(omega-aminoalkyl)-thiazole (V$_c$). Alkaline hydrolysis with an alkali metal hydroxide followed by treatment with a dilute hydrochloric acid can also be used. This primary amine product (Vc) corresponds to the starting material (V$_a$) produced by flow chart A and can undergo each of the reactions set forth in Flow Charts B-F to produce the compounds of this invention wherein Z in formula XX is CH$_2$.

In the above reaction schemes, the aminoalkyl group present at position 2 of the thiazole ring has been shown as carrying through each of the reaction steps essentially unchanged from the starting material employed (I in Flow Chart A). At times it is desirable to use certain alternate procedures in those instances where either R[1] or R[2] or both are hydrogen. For example, where R[1] is hydrogen but R[2] is alkyl, it is possible to use a benzyl protecting group through a given reaction scheme to the preparation of the hydroxymethyl derivative (IV) at which point the benzyl group can be removed by catalytic hydrogenation to give a secondary amine grouping NHR[2]. Similarly, an acyl protecting group can be used such as a benzoyl group and this protecting group is removed by reduction to an alcohol during the lithium triethylborohydride reduction step by using excess borohydride. Similarly, if it is desired to have a primary alkylamino group at position 2 of the thiazole ring, a protecting group such as a phthalimido group can be utilized. In such instance, the starting material (I) would be one in which R[1] and R[2], when taken together with the nitrogen to which they are attached, form a phthalimido group. This grouping can be carried throughout the synthetic procedure until it is desired to remove it (after reaction of the ethylamine to form the side chain) by hydrolysis as with hydrazine. Such a protecting group would be particularly valuable in those instances where it is desired to utilize a 4-chloromethylthiazole as an intermediate and to prepare such intermediate by the action of thionylchloride. In the preferred synthetic procedure set forth in Flow Chart A, such protecting groups for a secondary aminoalkyl group at position 2 of the thiazole ring is not necessary.

An alternate procedure for preparing intermediate useful in the synthesis of compounds of this invention (XX) starts with the reaction of dichloroacetone and a substituted aminothioacetamide. The use of the resulting 4-chloromethylthiazole where not more than one of $R^1$ and $R^2$ is H has been discussed previously in connection with Flow Chart A. However, this procedure is illustrated in Flow Chart H below and is particularly valuable in preparing the compounds of this invention wherein both $R^1$ and $R^2$ are H.

Flow Chart H

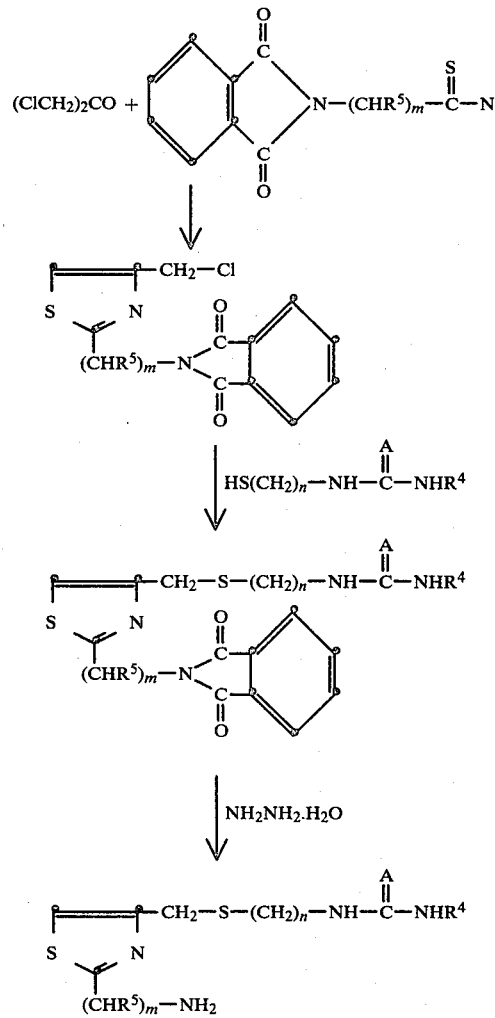

wherein $R^4$, $R^5$, A, m and n have then previously assigned significances.

In Flow Chart H, a 2-(phthalimidoalkylthioacetamide) reacts with dichloro acetone, following the procedure of *J. Am. Chem. Soc.*, 64, 90 (1942), to yield a 2-(phthalimidoalkyl)-4-chloromethylthiazole (XVIII). Reaction of this intermediate with a cysteamine (or homocysteamine) derivative in which the amine group is substituted so as to form a desired terminal "amidine" provides a 2-(phthalimido)-4-thiazolyl derivative XVIII which can be hydrolyzed with hydrazine to yield the 2-aminoalkylthiazole derivative (XX in which $R^1$ and $R^2$ are H, Z is S, and A and $R^4$ have their previous scope). Compounds in which Z is O are prepared similarly.

In the above structures, the guanidines and ethenediamine terminal groups have been written with structures K and L since it has been believed that these are the most probable structures

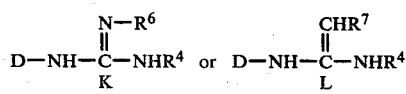

where D is

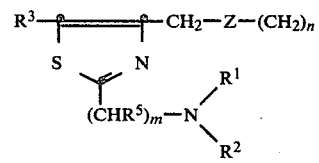

However, as is recognized in the art that K and L represent only one of three possible tautomeric structures, the others being K', K", L' and L".

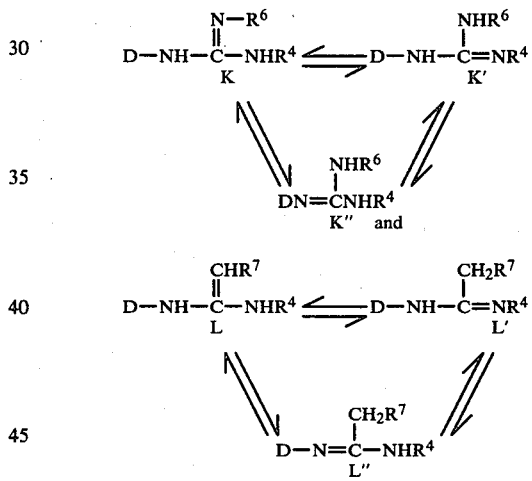

In the above formulas $R^1$, $R^2$, $R^3$, $R^4$, $R^5$, $R^6$, Z, m and n have the same meaning previously assigned and $R^7$ is $NO_2$, $SO_2$-$CH_3$ or $SO_2$-aryl. It is understood in the art that such tautomeric forms exist in equilibrium and, depending on the $R^4$, $R^6$, $R^7$ etc. substituent, one form may be more favored in a given substitution pattern. It is also understood that portrayal of a given tautomer in a structure is for convenience only and that all tautomeric forms are included in each such written structure.

This invention is further illustrated by the following examples.

EXAMPLE 1

Preparation of Ethyl 2-(Dimethylaminomethyl)-4-thiazolecarboxylate

A reaction mixture was prepared containing 15.5 g of dimethylaminothioacetamide hydrochloride, 20.5 g. of ethyl bromopyruvate and 100 ml. of ethanol. The reaction mixture was heated to refluxing temperature for about four hours after which time the solvent was removed in vacuo in a rotary evaporator. The residue, containing ethyl 2-(dimethylaminomethyl)-4-thiazolecarboxylate formed in the above reaction, was dissolved in a mixture of ether and water. The aqueous layer was separated. The ether layer was extracted with an equal volume of water and then discarded. The two aqueous layers were combined and washed with ether. The ether layer was again discarded and the aqueous layer cooled to a temperature in the range of 0°–5° C. Solid potassium carbonate was added until the aqueous layer gave a basic reaction to litmus. An oil separated comprising ethyl 2-(dimethylaminomethyl)-4-thiazolecarboxylate free base. The oily layer was extracted with ether and the ether extract separated and dried. The ether was removed by evaporation in vacuo. The resulting residue was purified by gradient high pressure liquid chromatography over silica using a toluene-ethyl acetate eluant. Ethyl 2-(dimethylaminomethyl)-4-thiazolecarboxylate thus obtained had the following physical characteristics:

Analysis Calculated: C, 50.45; H, 6.59; N, 13.07; S, 14.96; Found: C, 50.13; H, 6.39; N, 12.89; S, 15.04.

The nmr spectrum in CDCl$_3$ (TMS internal standard) gave the following signals ($\delta$): 1.43 (triplet, 3H), 2.40 (singlet, 6H), 3.87 (singlet, 2H), 4.47 (quartet, 2H), 8.20 (singlet, 1H).

Following the above procedure, a solution containing 20.4 g. of ethyl bromopyruvate and 20.8 g. of N-methyl-N-benzoyl thioacetamide in 100 ml. of ethanol was heated to refluxing temperature for about 4 hours. The solvent was removed by evaporation in vacuo and the resulting residue dissolved in 65 ml. of 4.5 N aqueous hydrochloric acid. The aqueous acidic layer was extracted with ether and the ether extract discarded. 11.5 g. of sodium carbonate were added to the aqueous layer. Ethyl 2-(methylbenzoylaminomethyl)-4-thiazolecarboxylate formed in the above reaction, being insoluble in the solution, separated and was extracted into ether. The ether extract was separated and dried. Evaporation of the ether yielded 20.2 g. of ethyl 2-(methylbenzoylaminomethyl)-4-thiazolecarboxylate melting at about 151.5°–153.5° C. after recrystallization from ethyl acetate.

Analysis Calculated: C, 59.19; H, 5.30; N, 9.20; Found: C, 58.98; H, 5.25; N, 8.90.

The nmr spectrum in CDCl$_3$ (TMS internal standard) gave the following signals ($\delta$): 1.42 (triplet, 3H), 3.07 (singlet, 3H), 4.41 (quartet, 2H), 4.98 (singlet, 2H), 7.40 (apparent singlet, 5H), 8.16 (singlet, 1H).

EXAMPLE 2

Preparation of
2-(Dimethylaminomethyl)-4-thiazolemethanol

A solution of 12.5 g. of ethyl 2-(dimethylaminomethyl)-4-thiazolecarboxylate dissolved in about 35 ml. of anhydrous tetrahydrofuran was prepared and then cooled to about 0° C. under a nitrogen atmosphere. About 130 ml. of a 1 molar solution of lithium triethylborohydride in THF was added in dropwise fashion while maintaining the temperature in the range 0°–5° C. The reaction mixture was stirred for about two hours after which time 36 ml. of 6 N aqueous hydrochloric acid were added while maintaining the temperature in the range −3° C. to 0° C. The volatile constituents were removed in vacuo on a rotary evaporator. Water was added to the resulting residue and again the volatile constituents were removed. Water was again added to the residue and the aqueous mixture extracted several times with ether. The ether extracts were separated and discarded. The aqueous solution was then chilled and made basic by the addition of solid potassium carbonate. The resulting alkaline aqueous mixture was extracted with ethyl acetate. 2-(Dimethylaminomethyl)-4-thiazolemethanol, being insoluble in the basic solution, separated and was extracted with several portions of ethyl acetate. The ethyl acetate extracts were combined, and the combined extracts washed with saturated aqueous sodium chloride and then dried. The ethyl acetate was removed by evaporation. The residue consisting of a brown oil weighing about 7.7 g. comprised 2-(dimethylaminomethyl)-4-thiazolemethanol formed in the above reaction having the following physical and chemical characteristics.

Analysic Calculated: C, 48.81; H, 7.02; N, 15.26; Found: C, 48.71; H, 6.77; N, 15.85.

The nmr spectrum in CDCl$_3$ (TMS internal standard) gave the following signals ($\delta$): 2.33 (singlet, 6H), 3.74 (singlet, 2H), 4.32 (singlet, 1H), 4.72 (singlet, 2H), 7.15 (singlet, 1H)

Boiling point=102° C. at 0.5 torr.

Following the above procedure, 22.5 g. of ethyl N-methyl-N-benzoyl 2-aminomethyl-4-thiazolecarboxylate were dissolved in 125 ml. of dry THF under a nitrogen atmosphere. 320 ml. of a 1 M LiEt$_3$BH in THF was added. (Excess borohydride was required over the amount in the above example because of the necessity of reducing both the ethyl ester group to a hydroxymethyl group and of removing the benzoyl group as benzyl alcohol leaving a secondary amine). The reaction mixture was worked up in accordance with the above procedure by decomposition with 6 N aqueous hydrochloric acid and water. The residue remaining after the volatile constituents had been removed was a thick oil which was taken up in a little water and 60 ml. of ether. 1 ml. of 12 N aqueous hydrochloric acid was added, thus making the aqueous phase strongly acidic. The ether layer was separated and the aqueous layer extracted five more times with equal portions of ether. The ether extracts were discarded. The water layer was separated and the water removed by evaporation in vacuo. The acidic residue was made strongly basic (while being cooled) with 50% aqueous sodium hydroxide (6 grams in 6 ml. of water). 2-Methylaminomethyl-4-thiazolemethanol produced by the above series of reactions was insoluble in the alkaline layer and separated. The compound was taken up in ethyl acetate using a continuous extractor. Removal of the solvent left a tannish oily residue weighing 10.7 grams comprising 2-methylaminomethyl-4-thiazolemethanol. The compound was converted to the dihydrochloride salt by standard laboratory procedures.

EXAMPLE 3

Preparation of
2-([2-(Dimethylaminomethyl)-4-thiazolyl)]methylthio)ethylamine

A reaction mixture was prepared from 18.8 g. of 2-dimethylaminomethyl-4-thiazolemethanol, 12.8 g. of 2-aminoethanethiol hydrochloride(cysteamine hydrochloride) and 160 ml. of 48% aqueous hydrobromic acid. The reaction mixture was stirred at about 100° C. for about 11 hours. The volatile constituents were removed in vacuo on a rotary evaporator. Water was added and the volatile constituents again removed by evaporation. The resulting residue, comprising 2-([2-

(dimethylaminomethyl)-4-thiazolyl])methylthio)ethylamine trihydrobromide formed in the above reaction, was dissolved in ethanol. The ethanol was evaporated and the resulting residue again dissolved in ethanol. Evaporation of the ethanol yielded a hygroscopic residue which was recrystallized from a methanol-ethyl acetate solvent mixture. 2-([2-(Dimethylaminomethyl-4-thiazolyl)]methylthio)ethylamine trihydrobromide thus prepared had the following physical and chemical characteristics:

Analysis calculated: C, 22.80; H, 4.25; Br, 50.56 N, 8.86; S, 13.53; Found: C, 23.02; H, 4.31; Br,50.64; N, 8,80; S, 13.60.

The nmr spectrum in DMSOd$_6$ (TMS internal standard) gave the following signals ($\delta$): 2.55–3.2 (multiplet, 4H), 2.84 (singlet 6H), 3.92 (singlet, 2H), 4.74 (singlet, 2H), 7.2–7.7 (broad, 1H), 7.94 (singlet, 1H), 7.92 (broad, 3H), 10.22 (broad, 1H).

Following the above procedure, 10.1 millimoles of 2-(methylaminomethyl)-4-thiazolemethanol dihydrochloride, 1.15 g. of cysteamine hydrochloride and 15 ml. of 48% aqueous hydrobromic acid were stirred at about 100° C. for about 7.5 hours. Water and hydrobromic acid were removed on a rotary evaporator and the resulting residue comprising 2-([2-(methylaminomethyl)-4-thiazolyl]methylthio)ethylamine trihydrobromide formed in the above reaction was dissolved in water and the water removed by evaporation. The residue was again taken up in water and the water removed by evaporation. The residue was then dissolved in a small volume of water and a solution of 5.5 g. of potassium carbonate in 15 ml. of water was added. The resulting alkaline solution was evaporated to dryness. The resulting residue, comprising the free base of 2-([2-(methylaminomethyl)-4-thiazolyl]methylthio)ethylamine, was slurried with ethanol and the ethanol separated and removed by evaporation. The residue was twice slurried with isopropanol. The residue was next extracted with boiling isopropanol several times and the combined isopropanol extracts combined and filtered. Removal of the isopropanol yielded a yellow oil. The yellow oil was dissolved in chloroform and the chloroform solution filtered. Chloroform was evaporated from the filtrate to yield 1.59 g. of a yellow oil comprising 2-([2-(methylaminomethyl)-4-thiazolyl]methylthio)ethylamine. The compound had the following physical characteristics:

The nmr spectrum is CDCl$_3$ (TMS internal standard) gave the following signals ($\delta$): 1.53 (overlapping singlets, 3H), 2.53 (singlet 3H), 2.62 (triplet, 2H), 2.86 (triplet, 2H), 3.81 (singlet, 2H), 4.04 (singlet, 2H), 7.04 (singlet, 1H).

EXAMPLE 4

Preparation of
N-methyl-N'-2-([2-(dimethylaminomethyl)-4-thiazolyl]-methylthio)ethyl-N"-cyanoguanidine A solution was prepared from 3.07 g. of dimethylcyanodithioimidocarbonate and 35 ml. of ethanol. A second solution containing 4.62 g. of 2-([2-(dimethylaminomethyl)-4-thiazolyl]methylthio)ethylamine in 50 ml. of ethanol was added in dropwise fashion with stirring to the first solution over a period of about 1.5 hours. The resulting reaction mixture was stirred for an additional 20 hours after which time the volatile constituents were removed in a rotary evaporator. Chromatography of the residue over silica by gradient elution using ethyl acetate containing increasing quantities of methanol as the eluant yielded fractions containing methyl N-2-([2-(dimethylaminomethyl)-4-thiazolyl]methylthio)ethyl-N'-cyanocarbamidothioate, formed in the above reaction. These fractions were combined and the solvent removed from the combined fractions in a rotary evaporator. The residue weighed 4.8 g. and, after recrystallization from carbon tetrachloride, melted at about 75°–77° C.

Analysis Calculated: C, 43.74; H, 5.81; N, 21.25; S, 29.19; Found: C, 43.46; H, 5.71; N, 20.98 S, 29.15.

2.52 g. Of the above thioester were dissolved in 12 ml. of methanol. 30 ml. of a 35% solution of methylamine (w/w) in ethanol was added with stirring. After five hours, the solvent and excess amine were removed by evaporation on a rotary evaporator. The residue was purified by chromatography over silica using gradient elution with an ethyl acetate-methanol solvent mixture as the eluant. Fractions containing N-methyl-N'-2-([2-(dimethylaminomethyl)-4-thiazolyl]methylthio)ethyl-N"-cyanoguanidine formed in the above reaction were combined to yield 1.86 g. of a glassy residue upon evaporation of the solvent.

Analysis Calculated: C, 46.13; H, 6.45; N, 26.90; Found: C, 46.43; H, 6.39; N, 26.85.

The nmr spectrum in CDCl$_3$ (TMS internal standard) shows the following signals ($\delta$): 2.34 (singlet, 6H); 2.72 (triplet, 2H); 2.84 (doublet, 3H); 3.42 (multiplet, 2H); 3.74 (singlet, 2H); 3.82 (singlet, 2H); 6.08 (multiplet, 1H); 6.22 (multiplet, 1H); 7.10 (singlet, 1H).

Following the above procedure, but substituting ethylamine for methylamine in the reaction with N-2-([2-(dimethylaminomethyl)-4-thiazolyl]methylthio)ethyl-N'-cyanocarbamidothioate, N-ethyl-N'-2-([2-(dimethylaminomethyl)-4-thiazolyl]methylthio)ethyl-N"-cyanoguanidine was prepared.

Analysis calculated for $C_{13}H_{22}N_6S_2$: C, 47.82; H, 6.79; N, 25.74; S, 19.64; Found: C, 48.05; H, 7.01; N, 25.51; S, 19.33.

The nmr in CDCl$_3$ (TMS internal standard) shows the following peaks ($\delta$): 1.22 (triplet, 3H), 2.34 (singlet, 6H), 2.72 (triplet, 2H), 3.1–3.55 (multiplets unresolved, 4H), 3.74 (singlet, 2H), 3.82 (singlet, 2H), 5.7 (broad, 1H), 6.0 (broad, 1H), 7.08 (singlet 1H).

EXAMPLE 5

Preparation of
N-2-([2-(dimethylaminomethyl)-4-thiazolyl]methylthio)ethyl-N'-methyl 2-nitro-1,1-ethenediamine.

A quantity of 2-([2-(dimethylaminomethyl)-4-thiazolyl)]methylthio)ethylamine trihydrobromide prepared from 50 g. of 2-(dimethylaminomethyl)-4-thiazolylmethanol by the procedure of Example 3 were dissolved in 150 ml. of water. A solution of 125 g. of potassium carbonate and 150 ml. of water was carefully added thereto. The water was removed by evaporation in vacuo. The resulting alkaline residue was triturated with ethanol and isopropanol and the alkanol removed therefrom by evaporation. The resulting residue was extracted several times with hot isopropanol and the isopropanol extracts were filtered to remove inorganic salts. Evaporation of the solvent from the filtrate yielded a residue which was dissolved in chloroform and filtered. The chloroform was removed from the filtrate on a rotary evaporator. The resulting residue, comprising the free base of 2-([2-(dimethylaminomethyl)-4-thiazolyl]methylthio)ethylamine, was dissolved in 250 ml. of water. This solution was added to a stirred suspension of 40.7 g. of N-methyl-1-methylthio-2-nitroethyleneamine (prepared according to the procedure of Belgian Patent 859,388) at 50° C. The solution was stirred at the same temperature for about 4 hours after the addition had been completed. Water was then removed by evaporation in vacuo on a rotary evaporator. The resulting residue was dissolved in ethanol and the solvent removed by evaporation. The residue was crystallized from an ethanol-acetonitrile solvent mixture and recrystallized from ethanol-ethyl acetate solvent mixture to yield 49.5 g. of N-methyl-N'-2-([2-(dimethylaminomethyl)-4-thiazolyl]methylthio)ethyl 2-nitro-1,1-ethenediamine melting at about 130°–132° C.

Analysis Calculated: C, 43.48; H, 6.39; N, 21.13 O, 9.65; Found: C, 43.66; H, 6.40; N, 21.14 O, 9.46.

The nmr spectrum in CDCl$_3$ (TMS internal standard) gave the following signals ($\delta$): 2.24 (singlet, 6H), 2.68 (triplet, 2H), 2.74 (singlet, 3H), 3.34 (multiplet, 2H), 3.70 (singlet, 2H), 4.84 (singlet, 2H), 6.46 (singlet, 1H), 7.16 (broad, 1H), 7.40 (singlet, 1H), 9.96 (broad, 1H).

Following the above procedure, 2-([2-(methylaminomethyl)-4-thiazolyl]methylthio)ethylamine and N-methyl-1-methylthio-2-nitroethyleneamine were reacted in water solution. The reaction was worked up and the product isolated by the above procedure to yield N-methyl-N'-2-([2-(methylaminomethyl)-4-thiazolyl]methylthio)ethyl 2-nitro-1,1-ethenediamine melting at 105°–107° C. after recrystallization from acetonitrile followed by recrystallization from ethanol.

Analysis Calculated: C, 41.62; H, 6.03; N, 22.06 O, 10.08; Found: C, 41.79; H, 6.10; N, 21.80; O, 10.28.

Following the above procedure, 2-([2-(dimethylaminomethyl)-4-thiazolyl]methylthio)ethylamine was caused to react with N-ethyl-1-methylthio-2-nitroethyleneamine to yield N-ethyl-N'-2-([2-(dimethylaminomethyl)-4-thiazolyl]methylthio)ethyl 2-nitro-1,1-ethenediamine melting at about 89°–90° C.

Analysis Calculated for $C_{13}H_{23}N_5O_2S_2$: C, 45.19, H, 6.71; N, 20.27; O, 9.26; Found: C, 45.32; H, 6.70; N, 20.44; O, 9.49.

EXAMPLE 6

Preparation of N-methyl-N'-2-([2-(dimethylaminomethyl)-4-thiazolyl]methylthio)ethylthiourea A solution was prepared containing 0.80 g. of 2-([2-(dimethylaminomethyl)-4-thiazolyl]methylthio)ethylamine and 0.29 g. of methylisothiocyanate in 10 ml. of ethanol. The solution was stirred at room temperature for about 17 hours after which time the solvent was removed by evaporation in vacuo. The residual gum, comprising N-methyl-N'-2-([2-(dimethylaminomethyl)-4-thiazolyl]methylthio)ethylthiourea formed in the above reaction, was purified by chromatography over silica using a gradient elution technique with ethyl acetate containing increasing quantities of methanol as the eluant. Fractions containing the above compound were combined and the solvent evaporated therefrom in vacuo, leaving as a residue 0.83 g. of a glassy solid.

Analysis Calculated: C, 43.39; H, 6.62; N, 18.40 S, 31.59; Found: C, 43.62; H, 6.49; N, 18.15; S, 31.70.

The nmr spectrum in CDCl$_3$ (TMS internal standard) gave the following signals ($\delta$): 2.34 (singlet, 6H), 2.80 (triplet, 2H), 3.00 (doublet, 3H), 3.74 (singlet, 2H), 3.82 (singlet, 2H), 3.6–3.9 (multiplet, 2H), 6.9 (broad, 1H), 7.08 (singlet, 1H), 7.2 (broad, 1H).

EXAMPLE 7

Preparation of N-methyl-N'-2-([2-(dimethylaminomethyl)-4-thiazolyl]methylthio)ethyl-N''-p-tolylsulfonylguanidine A suspension was prepared by adding 1.35 g. of dimethyl p-toluenesulfonylimidodithiocarbonate to 10 ml. of ethanol. While the suspension was being stirred at ambient temperature, a solution of 1.16 g. of 2-([2-(dimethylaminomethyl)-4-thiazolyl]methylthio)ethylamine in 10 ml. of ethanol was added over a 15 minute period. The reaction mixture was stirred for 2.5 hours after the addition had been completed. The solvent was then removed by evaporation in vacuo. The resulting residue was mixed with 20 ml. of a 35% solution (w/w) of ethanolic methylamine. This reaction mixture was stirred for about 15 hours after which time the solvent and other volatile constituents were removed by evaporation in vacuo. The residue was chromatographed over silica using a gradient elution technique employing ethyl acetate containing increasing quantities of methanol as the eluant. Fractions containing N-methyl-N'-2-([2-(dimethylaminomethyl)-4-thiazolyl]methylthio)ethyl-N''-p-tolylsulfonylguanidine formed in the above reaction were combined and the solvent removed therefrom to leave as a residue 1.9 g. of a glass.

Analysis Calculated: C, 48.95; H, 6.16; N, 15.86; O, 7.25; S, 21.78; Found: C, 49.25; H, 6.27; N, 16.10; O, 7.45; S, 21.62.

The nmr spectrum in CDCl$_3$ (TMS internal standard) gave the following signals ($\delta$): 2.34 (singlet, 6H), 2.38 (singlet, 3H), 2.62 (triplet, 2H), 2.80 (doublet, 3H), 3.35–3.55 (multiplet, greater than 2H), 3.72 (singlet, 2H), 3.74 (singlet, 2H), 7.06 (singlet, 1H), 7.18 (doublet, 2H), 7.70 (doublet, 2H).

EXAMPLE 8

Preparation of N-methyl-N'-2-([2-(dimethylaminomethyl)-4-thiazolyl]methylthio)ethyl-N''-nitroguanidine A reaction mixture was prepared containing 1.2 g. of 2-([2-(dimethylaminomethyl)-4-thiazolyl]ethylthio)ethylamine, 0.77 g. of S-methyl-N-methyl-N'-nitroisothiourea and 10 ml. of methanol. The reaction mixture was heated under reflux for 4.25 hours, after which time the solvent was removed by evaporation. The partially solid residue was chromatographed over silica using a gradient elution technique employing ethyl acetate containing increasing quantities of methanol as the eluant. Fractions shown by TLC to contain N-methyl-N'-2-([2-(dimethylaminomethyl)-4-thiazolyl]methylthio)ethyl-N''-nitroguanidine formed in the above reaction were pooled and the solvent removed from the pooled fractions. Trituration of the resulting residue with ether yielded a crystalline solid which, upon recrystallization from a methanol-ethyl acetate solvent mixture, yielded 0.83 g. of crystals melting at about 86.5°–88° C.

Analysis Calculated: C, 39.74; H, 6.06; N, 25.28; O, 9.62; S, 19.29; Found: C, 39.92; H, 5.89; N, 25.15; O. 9.38; S, 19.49.

EXAMPLE 9

Preparation of N-methyl-N'-2-([2-(dimethylaminomethyl)-5-methyl-4-thiazolyl]methylthio)ethyl 2-nitro-1,1-ethenediamine Following the procedure of Example 1, a reaction mixture containing 33.88 g. of ethyl 2-oxo-3-bromobutyrate [prepared by the procedure of Siefert et al., *Helv. Chim. Acta*, 33 725 (1950)], 21.52 g. of dimethylaminothioacetamide hydrochloride and 100 ml. of anhydrous ethanol was stirred and heated to refluxing temperature for about 2.5 hours. The reaction mixture was allowed to remain at room temperature overnight after which time it was concentrated by evaporation in vacuo. 100 ml. of an ice-water mixture was added to the resulting residue and the aqueous layer extracted with ethyl acetate. The ethyl acetate layer was discarded. The aqueous layer was cooled and then made basic (pH=11) with 2 N aqueous sodium hydroxide. The resulting alkaline layer was extracted several times with an equal volume of ethyl acetate and the ethyl acetate extracts were combined. The combined extracts were washed with water, with saturated aqueous sodium chloride, and were then dried. Concentration in vacuo provided a reddish oil comprising ethyl 2-(dimethylaminomethyl)-5-methyl-4-thiazolecarboxylate. Yield=21.2 g. (57%)

Two hundred milliliters of a one molar solution of lithium triethylborohydride in THF were cooled in an ice bath under a nitrogen atmosphere. A solution of 21.2 g. of ethyl 2-(dimethylaminomethyl)-5-methyl-4-thiazolecarboxylate in 60 ml. of THF was added in dropwise fashion over about 1.5 hours. The reaction mixture was maintained for an additional hour at 0° C. after which time it was decomposed by the cautious addition of 4 ml. of water plus 6 ml. of THF followed by 50 ml. of 6 N aqueous hydrochloric acid. The resulting reaction mixture was concentrated in vauco and the residue treated with water. Solid potassium carbonate was added to the aqueous mixture to pH=11. The resulting aqueous alkaline mixture was extracted several times with equal volumes of ethyl acetate. The ethyl acetate extracts were separated and combined and the combined extracts dried. The ethyl acetate was removed therefrom in vacuo to leave, as a residue, 2-(dimethylaminomethyl)-5-methyl-4-thiazolemethanol; yield=6.44 g. (44%).

Following the procedure of Example 3, a reaction mixture consisting of 6.4 g. of ethyl 2-(dimethylaminomethyl)-5-methyl-4-thiazolemethanol, 4.2 g. of cysteamine hydrochloride and 30 ml. of 48% aqueous hydrobromic acid was maintained at a temperature of about 100° C. under a nitrogen atmosphere for about 4 hours. The reaction mixture was cooled and the volatile constituents removed in vacuo. The resulting dark residue was twice trituated with ethanol and the ethanol removed by evaporation to remove residual HBr. The residue was then treated with 50 ml. of 5 N aqueous sodium hydroxide. The alkaline layer was continuously extracted with ether over an 18 hour period. The ether extract was dried and the ether removed therefrom in vacuo to provide 2-([2-(dimethylaminomethyl)-5-methyl-4-thiazolyl]methylthio)ethylamine prepared in the above reaction. The compound was a brown oil having the following physical characteristics: yield=1.38 g.

The nmr spectrum in CDCl$_3$ (TMS internal standard) shows the following peaks ($\delta$): 1.48 (singlet, 2H), 2.35 (singlet, 6H), 2.42 (singlet, 3H), 2.80 (multiplets, 4H), 3.72 (singlet, 2H), 3.80 (singlet, 2H).

Following the procedure of Example 5, a stirred solution of 1.38 g. of 2-([2-(dimethylaminomethyl)-5-methyl-4-thiazolyl]methylthio)ethylamine in 10 ml. of methanol was treated with N-methyl-1-methylthio-2-nitroethyleneamine. The reaction mixture was kept at room temperature overnight by which time all solids had dissolved. Thin layer chromatography over silica using a 10:10:1 ethyl acetate-methanol-ammonium hydroxide solvent system indicated substantially a single product. The reaction mixture was concentrated by evaporation of the methanol and the resulting gummy yellow residue was triturated with several portions of cold ether, thus providing an off-white gum. Repeated tritration with cold 1,2-dimethoxyethane yielded N-2-([2-(dimethylaminomethyl)-5-methyl-4-thiazolyl]methylthio)ethyl-N'-methyl-2-nitro-1,1-ethenediamine formed in the above reaction melting at about 104°–106° C.

Analysis Calculated: C, 45.19; H, 6.71; N, 20.27; Found: C, 45.54; H, 6.47; N, 19.60.

The compound had the following physical characteristics:

The nmr spectrum in CDCl$_3$ (TMS internal standard) shows the following peaks ($\delta$): 2.33 (singlet, 6H), 2.40 (singlet, 3H), 2.85 (multiplet, 2H), 2.97 (doublet, 3H), 3.48 (multiplet, 2H), 3.68 (singlet, 2H), 3.82 (singlet, 2H), 6.67 (singlet, 1H), 10.3 (broad, less than 2H).

EXAMPLE 10

Preparation of N-4-[2-(dimethylaminomethyl)-4-thiazolyl]butyl-N'-methyl 2-nitro-1,1-ethenediamine Following the procedure of Example 1, a stirred solution containing 3.2 g. of dimethylaminothioacetamide hydrochloride, and 6.48 g of bromomethyl 4-phthalimidobutyl ketone [prepared by the procedure of *Chem. Listy.*, 49, 1385 (1955); C.A., 50, 5573c (1956)]; in 50 ml. of ethanol was heated at refluxing temperature for about 5 hours and was then cooled. Volatile constituents were removed by evaporation in vacuo leaving 2-(dimethylaminomethyl)-4-(phthalimido-1-butyl)-thiazole as a semi-solid residue. The compound was utilized without further purification.

A solution was prepared containing the above product in 50 ml. of methanol. While the solution was being stirred, 2 ml. of 85% hydrazine hydrate were added and the resulting mixture heated to refluxing temperature for about 2 hours. At this point, an additional 2 ml. of 85% hydrazine hydrate were added and the heating continued for an additional two hours. The reaction mixture was then diluted with 4 volumes of water and the aqueous mixture made strongly basic with concentrated aqueous sodium hydroxide. The resulting alkaline layer was extracted continuously with ether for a 24 hour period. The ether extract was dried and the ether removed therefrom in vacuo to provide 4-[2-(dimethylaminomethyl)-4-thiazolyl]butylamine as a brown oil; weight=1.81 g. (42% yield from bromoketone). Mass spectrum: m/e at 152, 138, 128, 112, 96, 79, 71, 58, 42, 30 and 15.

A solution of 1.1 g. of the primary amine produced in the preceding step in 15 ml. of methanol was stirred while a solution of 3.20 g. of N-methyl 1-methylthio-2-nitroethyleneamine in methanolic solution was added thereto. The reaction mixture was maintained at room temperature for about 24 hours during which time evolution of methylmercaptan was noted. The progress of the reaction was followed by TLC. After the reaction had gone to completion according to TLC analysis, the volatile constituents were removed in vacuo and the resulting residue dissolved in a 9:1 ethyl acetate-methanol solvent mixture. This solution was placed on 15 g. of Woelm silica and the chromatogram developed with the same solvent mixture. Fractions shown by TLC to contain N-4-[2-(dimethylaminomethyl)-4-thiazolyl]butyl-N'-methyl 2-nitro-1,1-ethenediamine formed in the above reaction were combined and the solvent evaporated from the combined fractions in vacuo leaving a residual gum. Repeated trituration of this gum with small volumes of toluene followed by repeated recrystallization of the triturated solid from benzene provided off-white crystals melting at 97°–99° C.

Analysis Calculated: C, 49.82; H, 7.40; N, 22.35; S, 10.23; Found: C, 49.56; H, 7.25; N, 22.12; S, 9.95.

The compound had the following peaks by mass spectral analysis: m/e at 236, 212, 194, 178, 153, 126, 112, 97, 85, 71, 58, 42, 32 and 15.

EXAMPLE 11

Preparation of
N-methyl-N'-2-([2-(morpholinomethyl)-4-thiazolyl]methylthio)ethyl 2-nitro-1,1-ethenediamine Following the procedure of Example 1, morpholinothioacetamide hydrochloride was condensed with ethyl bromopyruvate to yield ethyl 2-(4-morpholinomethyl)-4-thiazolecarboxylate, melting at 129°–130° C. after recrystallization from a methylene dichloride-ethyl acetate solvent mixture.

Analysis Calculated: C, 51.54; H, 6.29; N, 10.93. Found: C, 51.36; H, 6.05; N, 10.88.

Following the procedure of Example 2, the above ester was reduced to the corresponding thiazolemethanol, 2-(4-morpholinomethyl)-4-thiazolemethanol, having an nmr spectrum in CDCl$_3$ (TMS internal standard) showing the following signals ($\delta$): 2.55 (multiplet, 4H), 3.35–3.90 (singlet plus multiplet, 6H), 4.70 (3H), 7.13 (singlet, 1H).

Reaction of the thiazolemethanol with cysteamine hydrochloride by the procedure of Example 5 yielded 2-([2-(4-morpholinomethyl)-4-thiazolyl]methylthio)ethylamine having the following physical characteristics: nmr spectrum in CDCl$_3$ (TMS internal standard) showing the following signals ($\delta$): 1.83 (singlet, 2H), 2.3–3.1 (multiplet, 8H), 3.4–3.9 (multiplet plus singlets, 8H), 7.03 (singlet, 1H).

Following the procedure of Example 5, the 2-[(4-thiazolyl)methylthio]ethylamine was reacted with N-methyl-1-methylthio-2-nitroethyleneamine to yield N-methyl-N'-2-([2-(4-morpholinomethyl)-4-thiazolyl]methylthio]ethyl-2-nitro-1,1-ethenediamine melting at 151°–153° C. after recrystallization from a methanolethyl acetate solvent mixture.

Analysis Calculated: C, 45.02; H, 6.21; N, 18.75. Found: C, 45.23; H, 6.24; N, 18.56.

EXAMPLE 12

Preparation of
N-methyl-N'-2-([2-(1-pyrrolidinomethyl)-4-thiazolyl]-methylthio)ethyl 2-nitro-1,1-ethenediamine The same sequence of reactions as in Example 11 were carried out starting with pyrrolidinomethylthioacetamide hydrochloride to yield the following intermediates.

Ethyl 2-(1-pyrrolidino)-4-thiazolecarboxylate. M.P.=81°–81.5° C. after recrystallization from a toluene-ethyl acetate solvent mixture.

The nmr spectrum in CDCl$_3$ (TMS internal standard) showed the following signals ($\delta$): 1.40 (triplet 3H), 1.82 (multiplet, 4H), 2.70 (multiplet, 4H), 4.02 (singlet, 2H), 4.45 (quartet, 2H), 8.17 (singlet, 1H).

2-(1-pyrrolidinomethyl)-4-thiazolemethanol. The nmr spectrum in CDCl$_3$ (TMS internal standard) gave the following signals ($\delta$): 1.77 (multiplex, 4H), 2.65 (multiplet, 4H), 3.92 (singlet, 2H), 4.73 (singlet, 3H), 7.15 (singlet, 1H).

2-([2-(1-pyrrolidinomethyl)-4-thiazolyl]methylthio)ethylamine trihydrobromide was crystallized from isopropanol.

The ethylamine obtained from the above hydrobromide was reacted with N-methyl-1-methylthio-2-nitroethyleneamine to yield N-methyl-N'-2-([2-(1-pyrrolidinomethyl)-4-thiazolyl]methylthio)ethyl recrystallization from a methanol-ethyl acetate solvent mixture.

Analysis calculated: C, 47.04; H, 6.49; N, 19.59. Found: C, 46.81; H, 6.55; N, 19.04.

EXAMPLE 13

Preparation of
N-methyl-N'-2-([2-(1-piperidinomethyl)-4-thiazolyl]methylthio)ethyl 2-nitro-1,1-ethenethiamine Following the sequence of reactions of Example 11, the following intermediates were produced from 1-piperidinothioacetamide hydrochloride.

Ethyl 2-(1-piperidinomethyl)-4-thiazolecarboxylate melting at 95°–97° C.

The nmr in CDCl$_3$ (TMS internal standard) gave the following signals ($\delta$): 1.40 (triplet, 3H), 1.53 (multiplet, 6H), 2.53 (multiplet, 4H), 3.85 (singlet, 2H), 4.45 (quartet, 2H), 8.20 (singlet, 1H).

2-(1-piperidinomethyl)-4-thiazolemethanol having an nmr spectrum in CDCl$_3$ (TMS internal standard) which gave the following signals ($\delta$): 1.53 (multiplet, 6H), 2.47 (multiplet, 4H), 3.77 (singlet, 2H), 4.77 (singlet, >3H), 7.13 (singlet, 1H).

2-([2-(1-piperidinomethyl)-4-thiazolyl]methylthio)ethylamine trihydrobromide crystallized from isopropanol. The nmr spectrum in DMSOd$_6$ (TMS internal standard) showed the following signals ($\delta$): 1.77 (multiplet, 6H), 2.6–3.8 (8H, multiplets), 3.97 (singlet, 2H), 4.80 (singlet, 2H), 7.80 (singlet, 1H), 8.12 (broad, 3H).

The primary amine obtained from the above salt was reacted with N-methyl 1-methylthio-2-nitroethyleneamine to yield N-methyl-N'-2-([2-(1-piperidinomethyl)-4-thiazolyl]methylthio)ethyl 2-nitro-1,1-ethenediamine melting at about 100°–103° C. after recrystallization from a methanol-ethyl acetate solvent mixture.

Analysis calculated: C, 48.49; H, 6.78; N, 18.85; Found: C, 48.72; H, 6.94; N, 18.64.

EXAMPLE 14

Preparation of
N-methyl-N'-2-([2-(methylethylaminomethyl)-4-thiazolyl]methylthio)ethyl 2-nitro-1,1-ethenediamine Following the reaction sequence of Example 11 starting with the reaction of N-methyl-N-ethyl aminothioacetamide hydrochloride and ethyl bromopyruvate, the following intermediates were prepared:

Ethyl 2-(methylethylaminomethyl)-4-thiazolecarboxylate, a non-crystalline oil.

2-(methylethylamiomethyl)-4-thiazolemethanol having an nmr spectrum in CDCl$_3$ (TMS internal standard) showing the following signals ($\delta$): 1.10 (triplet, 3H), 2.33 (singlet, 3H), 2.53 (quartet, 2H), 3.80 (singlet, 2H), 4.73 (singlet, 2H), 5.30 (singlet, 1H), 7.20 (singlet, 1H).

2-([2-(methylethylaminomethyl)-4-thiazolyl]methylthio)ethylamine having an nmr spectrum in CDCl$_3$ (TMS internal standard) showing the following signals (δ): 1.08 (triplet, 3H), 1.57 (singlet, 2H), 2.33 (singlet, 3H), 2.2–3.0 (multiplets, 6H), 3.78 (apparent singlet, 4H), 7.03 (singlet, 1H).

The above primary amine was reacted with N-methyl 1-methylthio-2-nitroethyleneamine to yield N-methyl-N'-2-([2-(methylethylaminomethyl)-4-thiazolyl]methylthio)ethyl 2-nitro-1,1-ethenediamine melting at 114°–116° C. after recrystallization from a methanol-ethyl acetate solvent mixture.

Analysis calculated: C, 45.19; H, 6.71; N, 20.27; Found: C, 45.48; H, 6.80; N, 19.98.

EXAMPLE 15

Preparation of N-methyl-N'-2-([2-dimethylaminomethyl)-4-thiazolyl]methylthio)ethyl-N''-aminocarbonylguanidine About 0.6 g. of N-methyl-N'-2-([2-(dimethylaminomethyl)-4-thiazolyl]methylthio)ethyl-N''-cyanoguanidine were dissolved in 8 ml. of 1.5 N aqueous hydrochloric acid. The resulting solution was allowed to remain at ambient temperature for about four days. Volatile constituents were then removed by evaporation in vacuo. The resulting residue, comprising N-methyl-N'-2-([2-(dimethylaminomethyl)-4-thiazolyl]methylthio)ethyl-N''-aminocarbonylguanidine dihydrochloride formed in the above reaction, was dissolved in ethanol and the ethanol removed by evaporation. The residue obtained thereby was recrystallized from isopropanol. The crystalline product was collected and digested with ethyl acetate. The ethyl acetate was removed by evaporation and the product obtained was crystallized from isopropanol to yield N-methyl-N'-2-([2-(dimethylaminomethyl)-4-thiazolyl]methylthio)ethyl-N''-aminocarbonylguanidine dihydrochloride melting at 156.5°–159.5° C.

Analysis Calculated for $C_{12}H_{23}Cl_2N_6OS_2$: C, 35.82; H, 5.76; Cl, 17.62; O, 3.98; Found: C, 35.64; H, 6.30; Cl, 17.73; O, 4.38.

In flow chart A above, compound I is a substituted aminothioacetamide hydrohalide of the structure

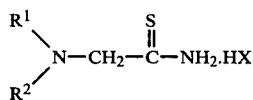

Where the substituting groups are alkyl, the compounds are known as, for example, dimethylaminothioacetamide, diethylaminothioacetamide, etc. and can be prepared by the method of *J. Org. Chem.*, (Russia), 6, 884 (1970) in English.

Illustrated preparations are given below.

PREPARATION 1

Morpholinothioacetamide

A reaction mixture was prepared from 203 ml. each of triethylamine and pyridine plus 63 g. of morpholinoacetonitrile. Hydrogen sulfide was bubbled through the heated, stirred reaction mixture for about 2.5 hours. Stirring was continued overnight at ambient temperature. The next day, H$_2$S was passed through the heated, stirred reaction mixture for an additional 1.5 hours. At this point, the solvents were evaporated in vacuo and the residue triturated with ether. The ether was discarded and the residue dissolved in ethanol. Crystalline morpholinothioacetamide precipitated and was separated by filtration. Treatment of the filtrate with alcoholic hydrogen chloride yielded morpholinothioacetamido hydrochloride melting in the range 64°–80° C. See also *J.A.C.S.*, 72, 2804 (1950).

Following the above procedure but using piperidinoacetonitrile in place of morpholinoacetonitrile, there was prepared piperidinothioacetamide hydrochloride melting at 166°–168° C., after recrystallization from ethylacetate. See also *Helv. Chim. Act.*, 43, 659 (1960).

Yield 35 g. from 62 g. of piperidinoacetonitrile starting material.

Following the above procedure using 100 g. of pyrrolidinoacetonitrile, there were obtained 68.4 g. of pyrrolidinothioacetamide hydrochloride (new) melting at about 195°–197° C.

Analysis calculated: C, 39.88; H, 7.25; N, 15.50 S, 17.74; Found: C, 39.66; H, 6.99; N, 15.76; S, 17.84.

Following the above procedure but using 49 g. of methylethylaminoacetonitrile, 200 ml. of triethylamine and 200 ml. of benzene, there was prepared N-methyl-N-ethylaminothioacetamide hydrochloride (new) melting at 115°–117° C.

The compounds of this invention are potent H$_2$ receptor antagonists and thus anti-ulcer agents. The relation of the H$_2$ receptors to mammalian gastric secretion is described in an article by Black et al. *Nature*, 236, 385 (1972).

The following assay for H$_2$ receptor blocking activity was employed. Female albino rats are treated with estrone 24 hours prior to the initiation of the experiment. The rats are sacrificed and the uterine horns removed therefrom and suspended at ambient temperatures in isolated organ baths containing De Jalon's solution. After equilibration, the uterine strips are exposed to 50 millimole aqueous potassium chloride, which produces a sustained contraction. When the uterus is so contracted, histamine produces a dose-dependent H$_2$ receptor-mediated relaxation. A control dose-response curve to histamine is constructed on each tissue. Following thorough washout of the histamine after obtaining the control dose-response curve, each antagonist (the compounds of this invention) is added for 30 minutes at a concentration of $10^{-5}$ molar. The uterine strips are then contracted with aqueous potassium chloride in the presence of the antagonist and a second dose-response curve to histamine obtained. In the presence of a competitive antagonist, the dose-response curve to histamine is shifted in parallel to the right with no depression of the maximum relative to the control curve. The dose ratio (DR) is calculated for each concentration of antagonist by dividing the ED$_{50}$ of histamine in the presence of the competitive antagonist by the control ED$_{50}$ for histamine. The dissociation constant (K$_B$) of the antagonist is calculated from the dose-ratios by the following equation:

$K_B$ = [antagonist]/(DR-1)

Cimetidine is included as an internal standard.

Results of the above assay carried out on N-methyl-N'-2-([2-(dimethylaminomethyl)-4-thiazolyl]methylthio)ethyl 2-nitro-1,1-ethenediamine indicated that the compound had an approximately 11 times higher affinity for the H$_2$ receptor than cimetidine. N-Methyl-N'-2-([2-(dimethylaminomethyl)-4-thiazolyl]methylthio)ethyl-N"-cyanoguanidine had an affinity of about 1.5 times greater than cimetidine. The $K_B$ for the former compound in nanomolar conc. was found to be 87 as compared to a $K_B$ for cimetidine of 871 indicating a relative affinity of about 10 to 1 using a Schild plot.

A second assay for $H_2$ receptor blocking activity employs the isolated bullfrog gastric mucosa—see Warrick and Lin, *Communications in Chem. Pathology and Pharmacology*, 13, 149 (1976). The assay is carried out as follows: The gastric mucosa of the bullfrog (*Rana catesbeiana*) is separated from the musculature of the stomach and placed between a pair of Ussing chambers made of lucite. The chambers are filled with frog Ringer solution and acid secretion is stimulated by addition of histamine to the serosal side of the mucosa at a final concentration of $10^{-5}$ M/l. Acid output is automatically titrated to pH 4.5. After steady response to $10^{-5}$ M/l of histamine is established, the antagonist (a compound of this invention) is added to the serosal chamber and the maximal inhibition by each concentration of the $H_2$-antagonist is recorded. From the dose-response curve, the $ED_{50}$ of the drug is calculated. The relative potency of each unknown antagonist is calculated by dividing the $ED_{50}$ for cimetidine by the $ED_{50}$ of the drug in question. N-methyl-N'-2-([2-(dimethylaminomethyl)-4-thiazolyl]methylthio)ethyl 2-nitro-1,1-ethenediamine had a relative potency of 17.78 compared to 1.0 for cimetidine.

An in vivo assay for antisecretory action of drugs on acid secretion utilizes gastric fistula dogs with vagally innervated gastric fistula and vagally denervated Heidenthain pouch. In this procedure, a steady-state gastric secretion is produced by the iv infusion of histamine. The antisecretory drugs under test are given either intravenously by infusion over a 30 minute period or orally 75 min. prior to collection of gastric secretion from the fistula. N-methyl-N'-2-([2-(dimethylaminomethyl)-4-thiaziolyl]methylthio)ethyl 2-nitro-1,1-ethenediamine was about 6.5 times as active as cimetidine by the intravenous route and about 11.0 times as active orally using this procedure.

These last results indicate that N-methyl-N'-2-([2-(dimethylaminomethyl)-5-thiazolyl]methylthio)ethyl 2-nitro-1,1-ethenediamine and other compounds of this invention are better absorbed orally than cimetidine or other recently developed histamine $H_2$ antagonists. This greater oral absorption is also indicated by a relatively greater oral toxicity (compared to iv toxicity) for the compounds of this invention. $LD_{50}$'s have been determined for the above ethenediamine and for cimetidine as follows: For N-methyl-N'-2-([2-(dimethylaminomethyl)-4-thiazolyl]methylthio)ethyl 2-nitro-1,1-ethenediamine, the following $LD_{50}$'s were obtained: mouse iv 265 mg/kg, mouse oral 1685 mg/kg; rat iv above 300 mg/kg, rat oral 1680 mg/kg. Literature $LD_{50}$'s for cimetidine are 150, 2600, 106 and 5000 mg/kg respectively. The relative lack (relative to cimetidine) of toxicity by the intravenous route of the compounds of this invention is surprising as is the greater oral absorption.

The above figures as to potency and toxicity indicate a favorable therapeutic ratio for the compounds of this invention. Preliminary tests also indicate that the compounds of this invention have a longer duration of action than cimetidine.

In utilizing the compounds of this invention as antisecretory agents, either the parenteral or oral route of administration may be employed. For oral dosage, a suitable quantity of a free base of this invention or a pharmaceutically-acceptable salt thereof formed with a non-toxic acid is mixed with one or more conventional excipients such as starch or other excipient and the mixture placed in telescoping gelatin capsules or compressed into tablets each containing from 100–400 mg. of active ingredients. The tablets may be scored if lower or divided dosages are to be used. For parenteral administration via an iv infusion, an isotonic solution of a salt is preferably employed through a soluble free base is also useful in iso-tonic preparations. However, the oral route is preferred.

Because of the higher oral absorption and longer duration of action of the compounds of this invention, particularly N-methyl-N'-2-([2-(dimethylaminomethyl)-4-thiazolyl]methylthio)ethyl 2-nitro-1,1-ethenediamine, it is believed that oral administration of about 50–80 mg. three to four times a day will suffice to control acid secretion in ulcer patients and thus alleviate ulcer symptoms. Generally, however, the compounds of this invention are administered to humans orally in a daily dosage range of 140–800 mg. Smaller dosages at more frequent intervals may also be employed. The preferred oral dosage range is about 2–5 mg./kg./day of mammalian body weight, although a dosage range of from 1–10 mg./kg./day can be used.

I claim:

1. A compound said compound being N-methyl-N'-([2-(dimethylaminomethyl)-4-thiazolyl]methylthio)ethyl 2-nitro-1,1-ethenediamine.

* * * * *

UNITED STATES PATENT AND TRADEMARK OFFICE
CERTIFICATE OF CORRECTION

PATENT NO. : 4,375,547
DATED : March 1, 1983
INVENTOR(S) : Richard P. Pioch

It is certified that error appears in the above-identified patent and that said Letters Patent are hereby corrected as shown below:

Column 5, line 66, "4-thiazly]me-" should read --4-thiazolyl]me- --.

Column 8, line 22, "2-nitroethaneamine" should read --2-nitroetheneamine--.

Column 9, line 68, "2-aylsulfonyl-" should read --2-arylsulfonyl- --.

Column 25, line 49, "methylthio]" should read --methylthio)--.

Column 26, line 5, "multiplex" should read --multiplet--; line 14, "rolidinomethyl)-4-thiazolyl]methylthio)ethyl recrystal-" should read --rolidinomethyl)-4-thiazolyl]methylthio)ethyl 2-nitro-1,1-ethenediamine melting at 119-120° C. after recrystal- --.

UNITED STATES PATENT AND TRADEMARK OFFICE
CERTIFICATE OF CORRECTION

PATENT NO. : 4,375,547

DATED : March 1, 1983

INVENTOR(S) : Richard P. Pioch

It is certified that error appears in the above-identified patent and that said Letters Patent are hereby corrected as shown below:

Column 29, line 43, "(dimethylaminomethyl)-5-" should read --(dimethylaminomethyl)-4- --.

Column 30, line 29, "through" should read --although--.

Claim 1, line 47, "A compound said compound being N-methyl-N'-" should read --A compound said compound being N-methyl-N'-2- --.

Signed and Sealed this

Sixteenth Day of August 1983

[SEAL]

Attest:

GERALD J. MOSSINGHOFF

Attesting Officer

Commissioner of Patents and Trademarks

UNITED STATES PATENT AND TRADEMARK OFFICE

CERTIFICATE EXTENDING PATENT TERM
UNDER 35 U.S.C. 156

Patent No.    : 4,375,547

Dated         : March 1, 1983

Inventor(s)   : Richard P. Poich

Patent Owner  : Eli Lilly and Company

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

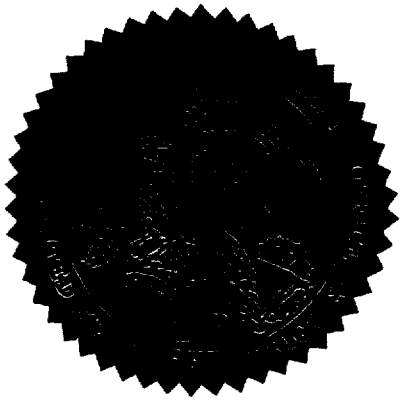

I have caused the seal of the Patent and Trademark Office to be affixed this Twentieth-seventh day of March 1989.

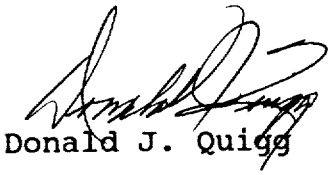

Donald J. Quigg

Assistant Secretary and Commissioner of Patents and Trademarks